(12) United States Patent
Hjelmgaard et al.

(10) Patent No.: US 9,976,958 B2
(45) Date of Patent: May 22, 2018

(54) METHOD FOR DETECTING CURING OF THE BINDER IN A MINERAL FIBER PRODUCT

(71) Applicant: Rockwool International A/S, Hedehusene (DK)

(72) Inventors: Thomas Hjelmgaard, Fredensborg (DK); Erling Lennart Hansen, Virum (DK)

(73) Assignee: ROCKWOOL INTERNATIONAL A/S, Hedehusene (DK)

( * ) Notice: Subject to any disclaimer, the term of this patent is extended or adjusted under 35 U.S.C. 154(b) by 0 days. days.

(21) Appl. No.: 15/102,612

(22) PCT Filed: Dec. 11, 2014

(86) PCT No.: PCT/EP2014/077400
§ 371 (c)(1),
(2) Date: Jun. 8, 2016

(87) PCT Pub. No.: WO2015/086756
PCT Pub. Date: Jun. 18, 2015

(65) Prior Publication Data
US 2016/0320303 A1 Nov. 3, 2016

(30) Foreign Application Priority Data
Dec. 11, 2013 (EP) .................................. 13196726

(51) Int. Cl.
*G01N 21/64* (2006.01)
*G01N 21/78* (2006.01)
(Continued)

(52) U.S. Cl.
CPC ....... *G01N 21/643* (2013.01); *G01N 21/6408* (2013.01); *G01N 21/78* (2013.01);
(Continued)

(58) Field of Classification Search
CPC ... G01N 2021/6432; G01N 2021/7786; G01N 2021/8472; G01N 21/643; G01N 21/78;
(Continued)

(56) References Cited

U.S. PATENT DOCUMENTS 4,582,520 A * 4/1986 Sturm ................ B29C 35/02
250/339.03
4,663,419 A 5/1987 Fugier et al.
(Continued)

FOREIGN PATENT DOCUMENTS

EP 0148050 A1 7/1985
WO 9938902 A1 8/1999
(Continued)

*Primary Examiner* — Jennifer Wecker
(74) *Attorney, Agent, or Firm* — Abel Law Group, LLP

(57) ABSTRACT

The present invention relates to a method for detecting curing and/or the local distribution of curing of the binder material, in particular for detection of anomalies of the cured binder, in a mineral fiber product. The present invention also relates to a reagent, in particular for use in such a method and the use of this reagent in the quality control of bonded mineral fiber products.

20 Claims, 20 Drawing Sheets

(51) Int. Cl.
*G01N 31/22* (2006.01)
*C03C 17/28* (2006.01)
*G01N 19/04* (2006.01)
*G01N 33/32* (2006.01)
*C08K 5/00* (2006.01)
*C03C 25/14* (2018.01)
*G01N 21/84* (2006.01)
*C09D 105/00* (2006.01)
*G01N 21/77* (2006.01)

(52) U.S. Cl.
CPC ............ *G01N 31/22* (2013.01); *C03C 17/28* (2013.01); *C03C 25/14* (2013.01); *C08K 5/0041* (2013.01); *C08L 2666/02* (2013.01); *C09D 105/00* (2013.01); *G01N 19/04* (2013.01); *G01N 21/6456* (2013.01); *G01N 21/8422* (2013.01); *G01N 33/32* (2013.01); *G01N 2021/6432* (2013.01); *G01N 2021/6439* (2013.01); *G01N 2021/7786* (2013.01); *G01N 2021/8472* (2013.01)

(58) Field of Classification Search
CPC ........... G01N 19/04; G01N 2021/6439; G01N 21/6408; C08L 2666/02; C08K 5/0041; C03C 17/28; C03C 25/14; C09D 105/00
See application file for complete search history.

(56) References Cited

U.S. PATENT DOCUMENTS

| | | | |
|---|---|---|---|
| 5,100,802 A * | 3/1992 | Mickols | G01N 21/6408 436/172 |
| 5,302,627 A * | 4/1994 | Field | C08F 2/46 522/13 |
| 6,017,983 A | 1/2000 | Gilleo | |
| 6,342,271 B1 | 1/2002 | Lericque | |
| 7,888,445 B2 | 2/2011 | Swift | |
| 8,197,587 B2 | 6/2012 | Jaffrennou et al. | |
| 2003/0065069 A1* | 4/2003 | Wojciak | C08K 5/0041 524/107 |
| 2003/0143268 A1* | 7/2003 | Pryce Lewis | A61J 3/10 424/464 |
| 2003/0224527 A1* | 12/2003 | Chen | C08J 3/248 436/155 |
| 2004/0149026 A1 | 8/2004 | Potyrailo et al. | |
| 2007/0027283 A1* | 2/2007 | Swift | C07H 5/04 527/312 |
| 2011/0026034 A1* | 2/2011 | Gauglitz | G01N 21/45 356/451 |
| 2011/0189492 A1* | 8/2011 | Gudik-Sorensen | C03C 25/26 428/435 |
| 2012/0037836 A1* | 2/2012 | Hansen | C03C 25/24 252/62 |
| 2012/0090505 A1 | 4/2012 | Jaffrennou et al. | |
| 2012/0144906 A1* | 6/2012 | Knyrim | G01N 31/222 73/73 |
| 2013/0059075 A1 | 3/2013 | Appley et al. | |
| 2013/0140481 A1 | 6/2013 | Naerum et al. | |
| 2013/0295813 A1 | 11/2013 | Hansen et al. | |
| 2014/0135430 A1 | 5/2014 | Naerum et al. | |
| 2014/0323618 A1 | 10/2014 | Appley et al. | |

FOREIGN PATENT DOCUMENTS

| | | |
|---|---|---|
| WO | 2007014236 A1 | 2/2007 |
| WO | 2009080938 A2 | 7/2009 |
| WO | 2011138458 A1 | 11/2011 |
| WO | 2012010694 A1 | 1/2012 |
| WO | 2012076462 A1 | 6/2012 |
| WO | 2013014076 A1 | 1/2013 |

* cited by examiner

METHOD FOR DETECTING CURING OF THE BINDER IN A MINERAL FIBER PRODUCT

FIELD OF THE INVENTION

The present invention relates to a method for detecting curing and/or the local distribution of curing of the binder material, in particular for detection of anomalies of the cured binder, in a mineral fibre product. The present invention also relates to a reagent, in particular for use in such a method and the use of this reagent in the quality control of bonded mineral fibre products.

BACKGROUND OF THE INVENTION

Mineral fibre products generally comprise man-made vitreous fibres (MMVF) such as, e.g. glass fibres, basalt fibres, slag wool, mineral wool and stone wool, which are bonded together by a cured thermoset polymeric binder material. For use as thermal or acoustical insulation products, bonded mineral fibre mats are generally produced by converting a melt made of suitable raw materials to fibres in conventional manner, for instance by a spinning cup process or by a cascade rotor process. The fibres are blown into a forming chamber and, while airborne and while still hot, are sprayed with a binder solution and randomly deposited as a mat or web onto a travelling conveyor. The fibre mat is then transferred to a curing oven where heated air is blown through the mat to cure the binder and rigidly bond the mineral fibres together.

One problem frequently encountered in the production of such mineral fibre products is an insufficient curing of the binder. Insufficient curing can for example occur in case there is an inhomogeneous binder distribution resulting in a high local concentration of binder which cannot be cured during the passage in the curing oven (5-10 minutes).

This phenomenon is termed "wet spots". Wet spots may result in poor performance of the installed product. The wet spot may diffuse into other surrounding building material, for example the mortar of external insulation and an unaesthetical spot may be seen on the outer wall because of the wet spot.

Insufficient curing may also occur throughout the whole product. This may be the case where the production line has a production change from one product type to another and where the curing settings needs to be changed. For example, changing from a low binder content product to a high binder content product, or vice versa. During the run-in of the line, the curing settings may not be optimal and insufficient curing occurs.

Another problem that can occur during the production of mineral fibre products are anomalies of the binder distribution like the agglomeration of large amounts of binder in a single part of the mineral fibre product (called "chewing gums").

Accordingly, there is a need for a method that allows the rapid detection of curing and/or the local distribution of curing of the binder material, and/or of anomalies of the cured binder in a mineral fibre product. Previously known methods for the detection involve the thorough inspection of the mineral fibre products in combination with reagents which chemically react with one or more of the components of the binder in order to allow a detection. These methods involve harmful chemicals and are therefore not convenient for a quick and efficient quality control of mineral fibre products.

In view of the foregoing, it would be a significant advancement in the art to provide a method for detecting curing and/or of the local distribution of curing of the binder material, and/or of anomalies of the cured binder, on a mineral fibre product that allows a rapid and secure detection. It would be a further advancement in the art if such a method could be performed without the use of harmful chemicals and without destroying the tested mineral fibre product.

SUMMARY OF THE INVENTION

It was an object of the present invention to provide a method for detecting curing and/or the local distribution of curing of the binder material, and/or of anomalies of the cured binder, and/or of anomalies of the binder on a mineral fibre product which allows a quick and efficient detection, and does not use harmful chemicals.

A further object of the present invention was to provide a reagent, in particular for use in such a method and the use of this reagent in the quality control of a production line of mineral fibre products.

In accordance with a first aspect of the invention, there is provided a method for detecting curing in a mineral fibre product comprising mineral fibres bonded together with a cured or partly cured thermoset binder, wherein the method comprises the step of bringing the mineral fibre product into contact with a liquid mixture comprising a fluorescent compound, and detecting the intensity of fluorescence and/or the pattern of fluorescence or absence of fluorescence on one or more surfaces of the mineral fibre product and/or detecting a color change on one or more surfaces of the mineral fibre product.

In accordance with a second aspect of the present invention, there is provided a reagent for the detection of curing and/or binder distribution anomalies in the mineral fibre product, such as binder distribution anomalies being agglomeration of binder in a mineral fibre product comprising mineral fibres bonded together by a cured thermoset binder, the reagent comprising a solution of 0.01 to 0.1 wt.-% fluorescein sodium salt in either of (1) an aqueous solution 1 to 30 wt.-%, in particular of 10 to 30 wt.-% ethanol or (2) an aqueous solution with a detergent.

In accordance with a third aspect of the present invention, there is provided a use of such a reagent for the quality control of a mineral fibre product.

DESCRIPTION OF THE PREFERRED EMBODIMENTS

The present inventors have surprisingly found that curing of the binder on a mineral fibre product can be detected by applying a fluorescent compound because the quenching of the fluorescence by the binder material is influenced by the curing. Without wanting to be bound by any specific theory, it is assumed that the mechanism for quenching of fluorescence might, for example, be due to pH effects, solubility effects and/or complex formation when the fluorescent substance comes into contact with the areas containing uncured binder.

For the purpose of the present invention, the term "cured or partly cured binder" refers to a binder which has at least been cured to a certain degree, e.g. by thermally treating in a curing apparatus, but has not necessarily been treated to achieve full curing in all regions of the product. Accordingly, the term "cured or partly cured binder" for the purpose of the present invention includes binders containing cured and uncured regions.

The inventive method is very easy to apply because it merely requires to bring the mineral fibre product into contact with the liquid mixture comprising a fluorescent compound and observe the presence or absence and/or pattern of fluorescence on the surface of the mineral fibre product and/or detecting a color change on the surface of the mineral fibre product, e.g. by visual inspection. There is no time delay associated with the detection method and the method can be applied to mineral products freshly made and just leaving the curing oven after cooling. Irregularities in curing or anomalies of the binder like "chewing gums" can therefore immediately be detected and the production process can therefore be re-adjusted quickly, thereby minimizing the wastage of inadequate products. In a preferred embodiment, the detection method is non-destructive. This is possible, because the fluorescent solution can generally be washed off after detection and does not change any essential properties of the product.

Fluorescent Compound

While in principal, any of the fluorescent compounds can be used in any amount in the method according to the present invention, particularly good results have been achieved when the liquid mixture comprises a fluorescent compound selected from the group consisting of
one or more xanthenes, such as fluorescein sodium salt, 2',7'-dichlorofluorescein, rhodamine B, rhodamine 6G, eosin Y disodium salt (2',4',5',7',-tetrabromofluorescein disodium salt), sulforhodamine B;
one or more acridines, such as acridine orange (3,6-bis (dimethylamino)acridine), acridine yellow G (3,6-di-amino-2,7-dimethylacridine hydrochloride);
quinine and/or one or more quinine derivatives, such as in form of a quinine containing tonic water;
one or more coumarins, such as umbelliferone (7-hydroxycoumarin);
one or more arylsulfonates, such as pyranine (8-hydroxy-pyrene-1,3,6-trisulfonic acid trisodium salt).

While in principal, a wide range of concentrations of the fluorescent compounds can be used, particularly good results have been achieved with a concentration of 0.001 to 1 wt.-%, in particular 0.01 to 0.5 wt.-%, in particular 0.01 to 0.1 wt.-%. In a preferred embodiment, the method is carried out by using a liquid mixture comprising a fluorescent compound in form of a solution of 0.001 to 1 wt.-%, in particular 0.01 to 0.1 wt.-% fluorescein sodium salt in either of (1) an aqueous solution of up to 30 wt.-%, in particular of 10 to 30 wt.-% of a $C_1$ to $C_4$ alcohol, in particular ethanol and/or isopropanol, (2) an aqueous solution with a detergent, (3) water.

In case of the use of fluorescein sodium salt in an aqueous solution of 10-30 wt.-% ethanol, it has been shown that using ethanol in this concentration range provides the best results because the fluorescein solution sufficiently wets the binder on the mineral fibre product and is still not absorbed by the binder material.

In case of the use of a fluorescein in an aqueous solution containing detergent, the detergent amounts of up to 5 wt.-%, in particular 1-5 wt.-%. Preferably, the detergent is soap (sodium and/or potassium salts of fatty acids).

Detection of Irregularities in the Curing of a Mineral Fibre Product

Curing oven surface: When sprayed with a fluorescein solution, a product not containing uncured regions produces a regular curing oven pattern of bright green fluorescence on an apparently black background. Areas with uncured regions give irregularities in this pattern.

Split surface: When a fluorescein solution is sprayed on otherwise visually hardly detectable wet spots or uncured areas, the surrounding area not containing uncured regions will fluoresce brightly green, while the wet spots, uncured areas and their saw-traces from the splitting process will appear black.

Detection of Regions with Uncured Binder in Mineral Fibre Products

Insufficient curing of the binder throughout the mineral fibre product will result in a lower intensity of fluorescence throughout the product. This can be visually detected, optionally by comparing the intensity of fluorescence with the intensity of fluorescence of a correctly cured product. Alternatively, the intensity of fluorescence can also be measured by an appropriate detector.

Detection of Anomalies of the Cured Binder on the Mineral Fibre Product

Agglomeration of large amounts of binder in a single part of the mineral fibre product ("chewing gums") can be detected since they will not fluoresce when brought into contact with the fluorescent spray.

The detection of such agglomerations of large amounts of binder in the product by the method according to the present invention is possible, presumably because such anomalies have a wet, uncured inner region, and are therefore detectable by the method which is sensitive to uncured binder areas.

FIG. 6 shows a flow chart for using the inventive method for the detection of uncured areas (wet spots) and binder agglomerations (chewing gums) in a mineral fibre product after bringing the product into contact with a fluorescein sodium salt solution. As can be seen from the flow chart, curing problems can be determined by a very simple procedure.

Binder

While there is no principal limitation of the inventive method to mineral fibre products bonded by specific binders, the method has shown particularly good results with certain binders.

PF-Resols

Very good results have been achieved for mineral fibre products bonded together by a cured thermoset binder, wherein the binder applied in the production of the mineral fibre product, in its non-cured state, comprises a conventionally used phenol-formaldehyde or phenol-urea-formal-dehyde (PUF) based resol and optionally a sugar component.

For these binders, without sugar component, reference is for example made to EP 0148050 and EP 0996653. For these binders, with sugar component, reference is made to WO 2012/076462. Binders based on alkanolamine-polycarbox-ylic acid anhydride reaction products Very good results have also been achieved for mineral fibre products bonded together by a cured thermoset binder, wherein the binder applied in the production of the mineral fibre product, in its non-cured state, comprises (1) a water-soluble binder component obtainable by reacting at least one alkanolamine with at least one polycarboxylic acid or anhydride and, optionally, treating the reaction product with a base; (2) a sugar component; and optionally (3) urea.

For these binders, reference is for example made to WO 2012/010694 and WO 2013/014076.

Other Binders

Very good results have also been achieved for mineral fibre products bonded together by a cured thermoset binder, wherein the binder applied in the production of the mineral fibre product, in its non-cured state, comprises
(a) a sugar component, and one or both of
(b) a polycarboxylic acid component, and
(c) a component selected from the group of amine compounds, ammonia, ammonium salts of a polycarboxylic acids, Examples of these binders are described in WO 2007/014236, WO 2011/138458 and WO 2009/080938.

For all the binders described above, the polycarboxylic acid component, if present, is preferably selected from dicarboxylic, tricarboxylic, tetracarboxylic, pentacarboxylic, and like polycarboxylic acids, and anhydrides, salts and combinations thereof.

For all the binders described above, the alkanolamine component, if present, is preferably selected from one or more of monoethanolamine, diethanolamine, triethanolamine, diisopropanolamine, triisopropanolamine, methyldiethanolamine, ethyldiethanolamine, n-butyldiethanolamine, methyldiisopropanolamine, ethylisopropanolamine, ethyldiisolpropanolamine, 3-amino-1,2-propanediol, 2-amino-1,3-propanediol, aminoethylethanolamine, and tris-(hydroxymethyl)-aminomethane.

For all the binders described above, the sugar component, if present, is preferably selected from sucrose, reducing sugars, in particular dextrose, poly-carbohydrates, and mixtures thereof, preferably dextrins and maltodextrins; more preferably glucose syrups, and more preferably glucose syrups with a Dextrose Equivalent value of DE=60-99.

Mineral Fibre Product

The mineral fibres employed may be any of man-made vitreous fibres (MMVF). In a preferred embodiment, the mineral fibre product comprises man-made vitreous fibres selected from stone wool, mineral wool, slag wool, basalt fibres, and glass fibres. These fibres may be present as a wool product, e.g. like a rock wool product.

Suitable fibre formation methods and subsequent production steps for manufacturing the mineral fibre product are those conventional in the art. Generally, the binder is sprayed immediately after fiberizing of the mineral melt on to the airborne mineral fibres. The aqueous binder composition is normally applied in an amount of 0.1 to 10%, preferably 0.2 to 8% by weight, of the bonded mineral fibre product on a dry basis.

The binder applied mineral fibre web is generally cured in a curing oven by means of a hot air stream. The hot air stream may be introduced into the mineral fibre web from below, or above or any combination of above or below in distinctive zones in the length direction of the curing oven.

Typically, the curing oven is operated at a temperature of from about 150° C. to about 350° C. Preferably, the curing temperature ranges from about 200 to about 300° C. Generally, the curing oven residence time is from 30 seconds to 20 minutes, depending on, for instance, the product density.

If desired, the mineral wool web may be subjected to a shaping process before curing. The bonded mineral fibre product emerging from the curing oven may be cut to a desired format e.g., in the form of a batt. Thus, the mineral fibre products produced, for instance, have the form of woven and nonwoven fabrics, mats, batts, slabs, sheets, plates, strips, rolls, granulates and other shaped articles which find use for example, as thermal or acoustical insulation materials, vibration damping, construction materials, facade insulation, reinforcing materials for roofing or flooring applications, as filter stock, as horticultural growing media and in other applications.

Means of Detection

A particular advantage of the method according to the present invention is that it can be integrated in a production process for mineral fibre products without delaying the process.

In a preferred embodiment of the inventive method, the steps of bringing the mineral fibre product into contact with a liquid mixture comprising a fluorescent compound and detecting absence of fluorescence and/or the pattern of fluorescence on one or more surfaces and/or detecting a color change on or more surfaces of the mineral fibre product are performed immediately, in particular between 1 to 500, more particular between 5 to 120 seconds, after the curing and cooling of the binder on the mineral fibre product.

A further advantage of the method according to the present invention is that the results can be obtained by simple visual inspection of the mineral fibre product immediately after bringing it into contact with the reagent. This visual inspection can take place without the help of special light conditions.

The contrast of the fluorescence can be strongly enhanced by performing the step of detection under the use of UV light. In a preferred embodiment, the step of detecting the pattern of fluorescence on one or more surfaces of the mineral fibre product therefore takes place under illumination with a UV light. Particularly good results are achieved by the use of a 254 nm UV light, i.e. a UV light that shows a strong emission in the range of 254 nm.

Application of the Reagent to the Mineral Fibre Product to be Tested

There is no principal limitation to the method of bringing into contact the reagent solution with the mineral fibre product to be tested. However, in a preferred embodiment of the method according to the present invention the reagent solution is brought into contact with a mineral fibre product by spraying the liquid on one or more surfaces of the mineral fibre product.

In one embodiment of the invention, the reagent solution is brought into contact with one or more of the outer surfaces of a mineral fibre product. This allows for the method of the present invention to be non-destructive for the mineral fibre product. It is possible to carry out the inventive method as a non-destructive method, because the fluorescent solution can generally be washed off after detection and does not change any essential properties of the product.

In an alternative embodiment, the fluorescent solution is applied to a split surface of the mineral fibre product. In this embodiment, the mineral fibre product is cut open and the fluorescent solution is applied to one or more of the surfaces resulting from the cut. This embodiment of the invention allows an inspection of the inner parts of the mineral fibre product.

In a preferred embodiment, the method according to the present invention is non-destructive for the mineral fibre product.

Reagent

The present inventors have tested a high number of liquid compositions containing different fluorescent compounds in order to evaluate the best combination for such a detection method.

Very good results have been achieved with a reagent comprising a solution of 0.001 to 1 wt.-% fluorescein sodium salt in either of (1) an aqueous solution of 1 to 30 wt. %, in particular 10 to 30 wt.-% of a $C_1$ to $C_4$ alcohol, in particular ethanol and/or isopropanol, (2) an aqueous solution with a detergent.

In a preferred embodiment, the reagent contains a solution of 0.01 to 0.1 wt.-% fluorescein sodium salt in either of (1) an aqueous solution of 1 to 30 wt.-%, in particular 10 to 30 wt.-% ethanol or (2) an aqueous solution with a detergent.

In a particularly preferred embodiment, the reagent comprises a solution of 0.01 wt.-% fluorescein sodium salt in 20 wt.-% ethanol. In an alternative preferred embodiment, the reagent comprises 0.01 wt.-% fluorescein sodium salt in an aqueous solution comprising 0.1 to 5 wt.-% detergent in form of soap (sodium and/or potassium salts of fatty acids).

Use of the Reagent

The reagent according to the present invention can be used for a quick and uncomplicated in-line testing of mineral fibre products in the production line for the detection of curing problems. The present invention is therefore also directed to the use of the inventive reagent for the quality control of a mineral fibre product.

BRIEF DESCRIPTION OF THE DRAWINGS

In the accompanying drawings,

FIGS. 2-1 to 2-4 are photographs of samples obtained by the procedure described in Example 2 below;

FIGS. 3-1 to 3-2 are photographs of samples obtained by the procedure described in Example 3 below;

FIGS. 4-1 to 4-3 are photographs of samples obtained by the procedure described in Example 4 below;

FIGS. 5-1 to 5-9 are photographs of samples obtained by the procedure described in Example 5 below;

FIGS. 5-10 to 5-12 are photographs of samples obtained by the procedure described in Example 6 below; and FIG. 6 is a schematic representation of an embodiment of the method of the present invention.

EXAMPLES

Figure 1:
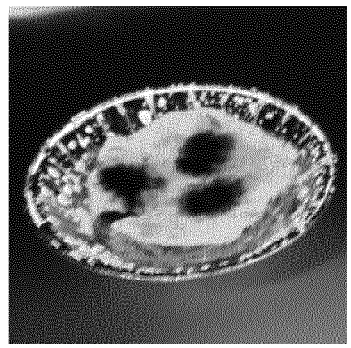
FIGS. 1-1 to 1-36 are photographs of samples obtained by the procedure described in Example 1 below.

Binders were made for the Examples below.
Binder: PUF-sugar
This binder is a PUF-resol with sugar.

A phenol-formaldehyde resin is prepared by reacting 37% aq. formaldehyde (606 g) and phenol (189 g) in the presence of 46% aq. potassium hydroxide (25.5 g) at a reaction temperature of 84° C. The reaction is continued until the acid tolerance of the resin is 4 and most of the phenol is converted. Urea (241 g) is then added.

Using the urea-modified phenol-formaldehyde resin obtained, a binder is made by addition of 25% aq. ammonia (90 mL) and ammonium sulphate (13.2 g) followed by either water (1.80 kg), dextrose syrup with a DE value of 90-95 (Cargill) (370 g), and 40% aq. silane (Momentive VS-142) (3.1 g) or water (2.48 kg), dextrose syrup with a DE value of 90-95 (909 g), and 40% aq. silane (Momentive VS-142) (4.3 g).

Binder: B1 and B1-urea-sugar

This binder is based on alkanolamine-polycarboxylic acid anhydride reaction products.

B1:

Diethanolamine (DEA, 280 g) is placed in a 1-liter glass reactor provided with a stirrer and a heating/cooling jacket. The temperature of the diethanolamine is raised to 60° C. where after tetrahydrophthalic anhydride (THPA, 156 g) is added. After raising the temperature and keeping it at 130° C., a second portion of tetrahydrophthalic anhydride (78 g) is added followed by trimellitic anhydride (TMA, 156 g). After reacting at 130° C. for 1 hour, the mixture is cooled to 95° C. Water (231 g) is added and stirring is continued for 1 hour. After cooling to ambient temperature, the mixture is poured into water (1.90 kg) and 50% aq. hypophosphorous acid (12 g), 25% aq. ammonia (131 g) and 50% aq. silane (Momentive VS-142) (2.9 g) are added under stirring.

B1-Sugar-Urea:

Diethanolamine (DEA, 157 g) is placed in a 5-liter glass reactor provided with a stirrer and a heating/cooling jacket. The temperature of the diethanolamine is raised to 60° C. where after tetrahydrophthalic anhydride (THPA, 87 g) is added. After raising the temperature and keeping it at 130° C., a second portion of tetrahydrophthalic anhydride (44 g) is added followed by trimellitic anhydride (TMA, 87 g). After reacting at 130° C. for 1 hour, the mixture is cooled to 95° C. Water (315 g) is added and stirring is continued for 1 hour. Urea (281 g) is then added and stirring is continued until all solids are dissolved. After cooling to ambient temperature, the mixture is poured into water (3.66 kg) and 50% aq. hypophosphorous acid (6 g) and 25% aq. ammonia (55 g) are added under stirring. Dextrose syrup with a DE value of 90-95 (Cargill) (1.54 kg) heated to 60° C. is then added under stirring followed by 50% aq. silane (Momentive VS-142) (6.2 g).

Example 1: Detecting Model B1 and B1-Sugar-Urea Wet Spots with Fluorescent Dyes in Demineralized Water, Absolute Ethanol or Mixtures Thereof A range of fluorescent dyes in different concentrations (0.01-1.0%) and solvents (demineralized water, absolute ethanol, or mixtures thereof) were tested for their response to model wet spots.

Small disc-shaped stone wool samples (diameter: 5 cm; height 1 cm) were cut out of stone wool and heat-treated at 580° C. overnight to remove all organics. Three spots of 0.5 mL B1 (no dextrose) or B1-sugar-urea (with dextrose) were made on each disc which were then dried at 105° C. for 30 min. The fluorescent dyes would give the same response on fully cured stone wool as on the heat-treated background on the model wet spot discs.

Solutions of fluorescein, fluorescein sodium salt, 2',7'-dichlorofluorescein, rhodamine B, rhodamine 6G, eosin Y disodium salt (2',4',5',7',-tetrabromofluorescein disodium salt), eosin B (4',5'-Dibromo-2',7'-dinitrofluorescein disodium salt), sulforhodamine B, acridine orange (3,6 bis (dimethylamino)acridine), acridine yellow G (2,7-dimethylacridine-3,6-diamine hydrochloride); tonic water (containing quinine), quinine hydrochloride dihydrate, umbelliferone (7-hydroxycoumarin), pyranine (8-hydroxypyrene-1,3,6-trisulfonic acid trisodium salt), were sprayed onto the stone wool discs with model wet spots and investigated under 365 nm UV-light, 254 nm UV-light and daylight.

The results are seen in table 1:

TABLE 1

| Dye | Conc. (%) | Solvent | Binder | Detection | Wet spot | Background | Cand.[a] | FIG. |
|---|---|---|---|---|---|---|---|---|
| Fluorescein sodium salt | 0.01 | Water or 20% EtOH | B1-sugar-urea | 254 nm | Black | Bright green | ++ | 1-01 |
| | 0.01 | Water | B1 | Daylight | Medium gray | Light green | + | 1-02 |
| | 0.1 | Water | B1 | 365 nm | Weak green | Bright green | + | 1-03 |
| | 0.1 | Water | B1 | 254 nm | Black | Bright green | ++ | 1-04 |
| | 0.1 | Water | B1 | Daylight | Medium gray | Light green | + | 1-05 |
| | 1.0 | Water | B1 | 365 nm | Bright green | Weak green | + | 1-06 |
| | 1.0 | Water | B1 | Daylight | Medium gray-green | Medium brown | + | 1-07 |
| 2',7'-Dichlorofluorescein | 0.01 | EtOH | B1-sugar-urea | 254 nm | Black | Medium green | + | 1-08 |
| Rhodamine B | 0.1 | Water | B1 | 365 nm | Bright orange | Weak orange | + | 1-09 |
| | 0.5 | Water or 20% EtOH | B1-sugar-urea | 365 nm | Orange | Dark brown | + | 1-10 |
| | 1.0 | Water | B1 | 365 nm | Bright red-orange | Black | ++ | 1-11 |
| Rhodamine 6G | 0.01 | water, 20% EtOH or EtOH | B1-sugar-urea | 254 nm | Black | Weak yellow | + | 1-12 |
| | 0.1 | Water | B1 | 365 nm | Bright yellow | Weak yellow | + | 1-13 |
| | 0.1 | Water | B1 | Daylight | Light green | Light pink | + | 1-14 |
| | 1.0 | Water | B1 | 365 nm | Bright yellow-orange | Black | ++ | 1-15 |
| Eosin Y disodium salt | 0.01 | 10% EtOH | B1-sugar-urea | 254 nm | Black | Weak green | + | 1-16 |
| | 0.1 | 10% EtOH | B1-sugar-urea | 254 nm | Faint green | Medium green | + | 1-17 |
| Sulforhodamine B | 0.1 | 10% EtOH | B1-sugar-urea | 254 nm | Black | Medium orange | + | 1-18 |
| | 1.0 | 10% EtOH | B1-sugar-urea | 365 nm | Bright orange | Weak orange | + | 1-19 |
| Acridine Orange | 0.01 | 10% EtOH | B1-sugar-urea | 254 nm | Weak green | Medium green | + | 1-20 |
| | 0.1 | 40% EtOH | B1-sugar-urea | 365 nm | Black | Weak green | + | 1-21 |
| | 0.1 | 40% EtOH | B1-sugar-urea | 254 nm | Black | Medium green | ++ | 1-22 |
| | 0.1 | 40% EtOH | B1-sugar-urea | Daylight | Brown-orange | Yellow-orange | + | 1-23 |
| Acridine Yellow G | 0.01 | 10% EtOH | B1-sugar-urea | 365 nm | Black | Faint blue-green | + | 1-24 |
| | 0.01 | 10% EtOH | B1-sugar-urea | 254 nm | Black | Weak blue-green | + | 1-25 |
| | 0.1 | 10% EtOH | B1-sugar-urea | 365 nm | Faint blue-green | Weak blue-green | + | 1-26 |
| | 0.1 | 10% EtOH | B1-sugar-urea | 254 nm | Black | Weak blue-green | + | 1-27 |
| Tonic water[b] | — | — | B1-sugar-urea | 254 nm | Black | Medium blue | + | 1-28 |
| Umbelliferone | 0.01 | 10% EtOH | B1-sugar-urea | 365 nm | Weak blue | Medium blue | + | 1-29 |
| | 0.01 | 10% EtOH | B1-sugar-urea | 254 nm | Black | Medium blue | ++ | 1-30 |
| | 0.1 | 10% EtOH | B1-sugar-urea | 254 nm | Black | Bright blue | ++ | 1-31 |
| Pyranine | 0.01 | 10% EtOH | B1-sugar-urea | 365 nm | Bright green | Medium green | + | 1-32 |
| | 0.01 | 10% EtOH | B1-sugar-urea | 254 nm | Weak green | Medium green | + | 1-33 |
| | 0.01 | 10% EtOH | B1-sugar-urea | Daylight | Gray-brown | Bright green | + | 1-34 |
| | 0.1 | 10% EtOH | B1-sugar-urea | 254 nm | Weak green | Bright green | + | 1-35 |
| | 0.1 | 10% EtOH | B1-sugar-urea | Daylight | Gray-brown | Bright green | + | 1-36 |
| None (comparative example) | 0 | none | B1-sugar-urea | 254 nm | Black | Black | comparative | — |

Key:
[a]++: very good candidate; +: good candidate.
[b]Soaked instead of spraying.

Fluorescein sodium salt represented the most promising candidate in these studies as a result of high level of contrast at low concentration (0.01-0.1%), possibility for detection at both 254 nm UV-light and daylight, no dependence on dextrose content in binder, high solubility in water, low toxicity and low price.

Example 2: Detecting Model B1-Sugar-Urea Wet Spots with 0.01% Fluorescein Sodium Salt in Alternative Solvents The sensitivity of 0.01% fluorescein sodium salt spray towards the nature of the water and alcohol used was investigated:

Small disc-shaped stone wool samples with three B1-sugar-urea (with dextrose) wet spots were obtained as described in example 1. Solutions of 0.01% fluorescein sodium salt in all six possible combinations of 20% absolute ethanol, denatured ethanol or isopropanol in deionized water or cold tap water were sprayed onto the stone wool discs with model wet spots and investigated under 254 nm UV-light and daylight.

Figures 1, 2:
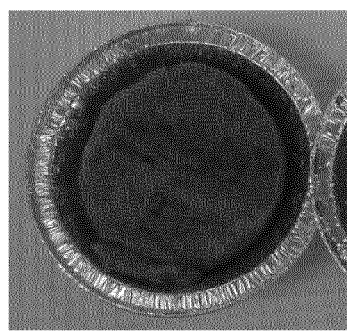
Figures 1, 2, 3:
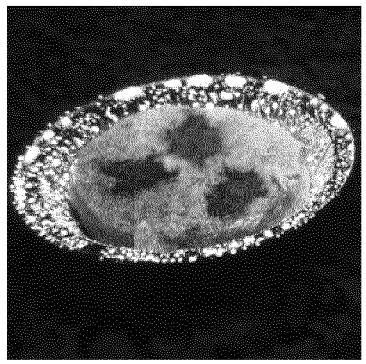
Figures 1, 2, 3, 4:
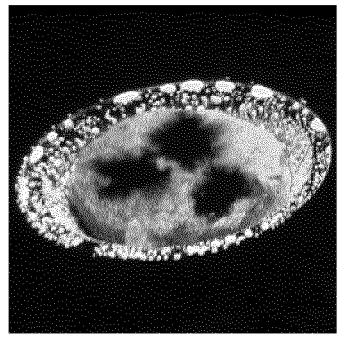

Results identical to those obtained in Example 1 were obtained with all solvent mixtures (FIG. 2-1 and FIG. 2-2 at 254 nm and FIG. 2-3 and FIG. 2-4 at daylight). No difference between the use of absolute ethanol, denatured ethanol or isopropanol in deionized water or cold tap water in sprays based on 0.01% fluorescein sodium salt.

Example 3: Detecting Model B1-Sugar-Urea Wet Spots with 0.01% Fluorescein Sodium Salt Water with 1-5% Detergent The possibility of substituting the use of alcohols with detergents to lower the surface tension of the spray was investigated:

Small disc-shaped stone wool samples with three B1-sugar-urea (with dextrose) wet spots were obtained as described in Example 1. Solutions of 0.01% fluorescein sodium salt in water with 1% or 5% detergent were sprayed onto the stone wool discs with model wet spots and investigated under 365 nm UV-light, 254 nm UV-light and daylight. As a detergent Suma Star Free, JohnsonDiversey, and Ecolab® Assert Clean were used and gave the same results.

FIGS. 3-1 and 3-2 show the examples where Suma Star Free, JohnsonDiversey were used.

Results identical to those obtained in Example 1 were obtained (FIG. 3-1 at 254 nm and FIG. 3-2 at daylight).

1% or 5% detergent can be used instead of 10-20% alcohol to lower the surface tension in sprays based on 0.01% fluorescein sodium salt.

Example 4: Detecting Model PUF-Sugar Wet Spots with 0.01% Fluorescein Sodium Salt The feasibility of using the fluorescein sodium salt based spray on products containing the PUF binder was studied:

Small disc-shaped stone wool samples with three 25% or 45% PUF-sugar (PUF-binder with 25% and 45% dextrose) model wet spots were obtained in a similar manner to the one described in Example 1, in this case by drying the stone wool discs with added binder at 80° C. for 1 h instead of at 105° C. for 30 min.

Solutions of 0.01% fluorescein sodium salt in 20% absolute ethanol in deionized water or in 20% isopropanol in cold tap water were sprayed onto the stone wool discs with model wet spots and investigated under 365 nm UV-light, 254 nm UV-light and daylight.

Results identical to those obtained in Example 1 were obtained (FIG. 4-1 with 25% dextrose left and 45% dextrose right at 365 nm, FIG. 4-2 at 254 nm and FIG. 4-3 in daylight).

0.01% fluorescein sodium salt can also be used to detect PUF-based wet spots and no sensitivity towards the nature of the solvent was observed.

Example 5: Detection of Curing on Outer Surface of Stone Wool Products with B1-Sugar-Urea Using 0.01% Fluorescein Sodium Salt 0.01% fluorescein sodium salt in 20% aqueous ethanol was tested on the outer surface of an acoustical ceiling product with regions of uncured binder, the binder being the B1-sugar-urea binder (after removing the fleece layer from the acoustical ceiling product). The areas with uncured regions appear as discrete "soft bumps" on the surface.

Figures 1, 2, 3, 4, 5:
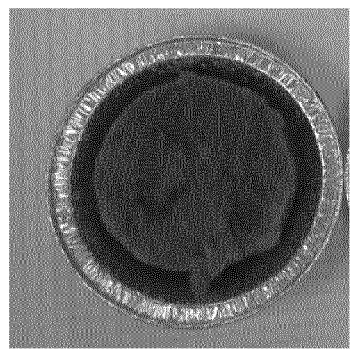

A product not containing uncured regions produced a regular curing oven pattern of bright green fluorescence on a apparently black background. The areas with uncured regions gave irregularities in this pattern (FIGS. 5-1 and 5-2).

0.01% fluorescein sodium salt in 20% aqueous ethanol was likewise tested on the outer surface of the areas with uncured regions of products with B1-sugar-urea binder.

Figures 1, 2, 3, 4, 5, 6:
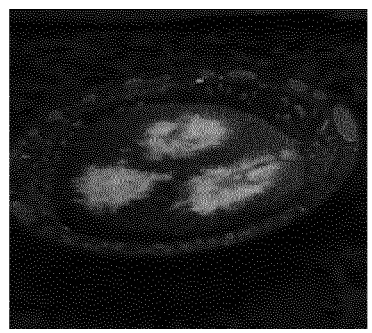
Figures 1, 2, 3, 4, 5, 6, 7:
Figures 1, 2, 3, 4, 5, 6, 7, 8:
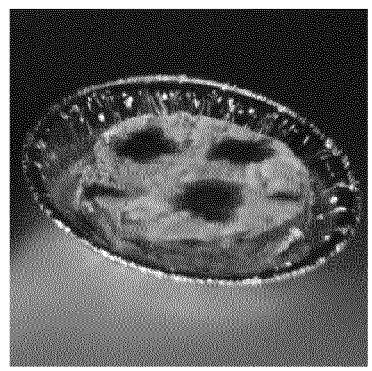
Figures 1, 2, 3, 4, 5, 6, 7, 8, 9:
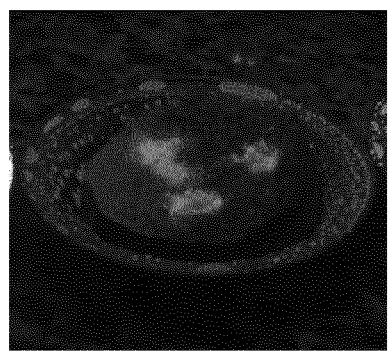
Figures 1, 2, 3, 4, 5, 6, 7, 8, 9, 10:
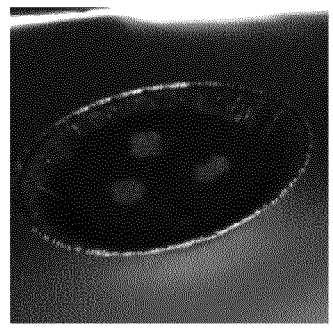
Figures 1, 2, 3, 4, 5, 6, 7, 8, 9, 10, 11:
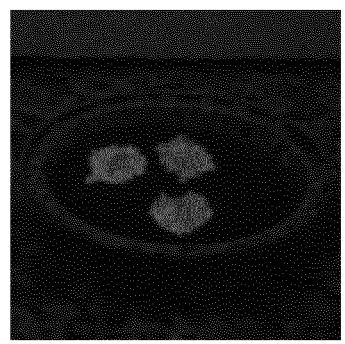
Figures 1, 2, 3, 4, 5, 6, 7, 8, 9, 10, 11, 12:
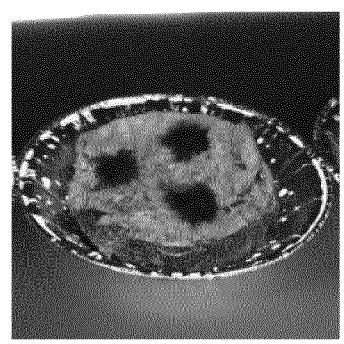
Figures 1, 2, 3, 4, 5, 6, 7, 8, 9, 10, 11, 12, 13:
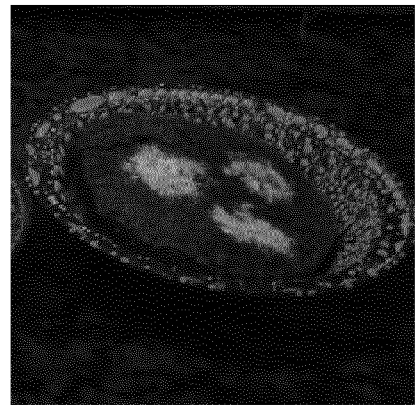
Figures 1, 2, 3, 4, 5, 6, 7, 8, 9, 10, 11, 12, 13, 14:
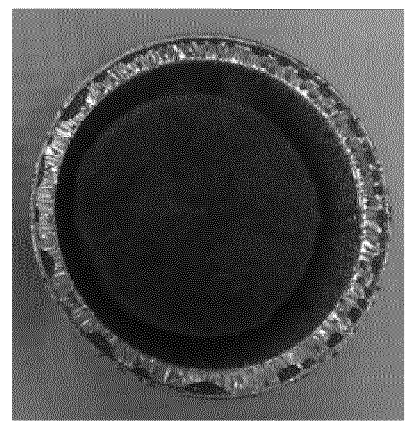
Figures 1, 2, 3, 4, 5, 6, 7, 8, 9, 10, 11, 12, 13, 14, 15:
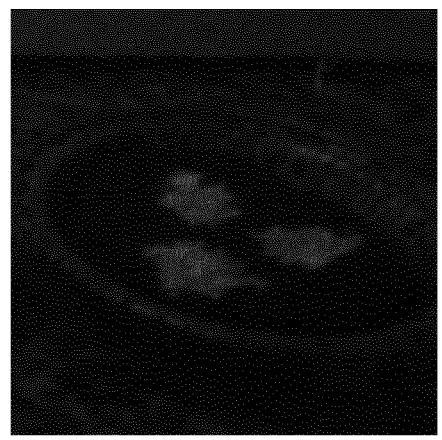
Figures 1, 2, 3, 4, 5, 6, 7, 8, 9, 10, 11, 12, 13, 14, 15, 16:
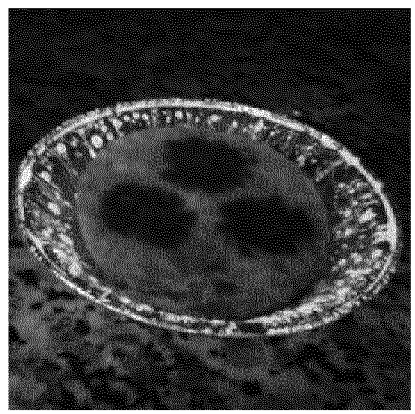
Figures 1, 2, 3, 4, 5, 6, 7, 8, 9, 10, 11, 12, 13, 14, 15, 16, 17:
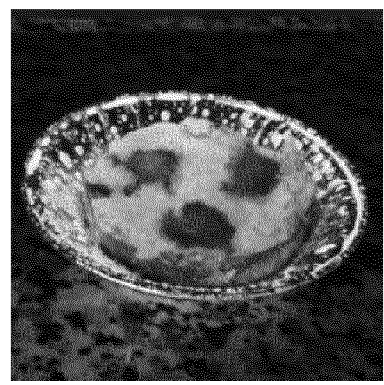
Figures 1, 2, 3, 4, 5, 6, 7, 8, 9, 10, 11, 12, 13, 14, 15, 16, 17, 18:
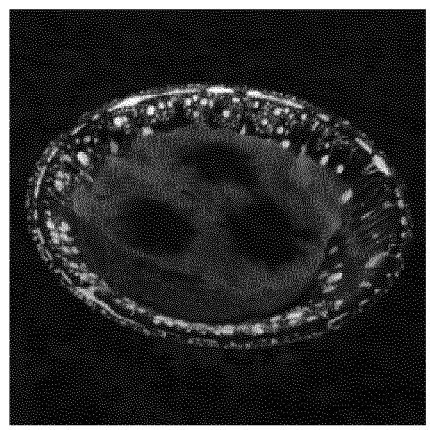
Figures 1, 2, 3, 4, 5, 6, 7, 8, 9, 10, 11, 12, 13, 14, 15, 16, 17, 18, 19:
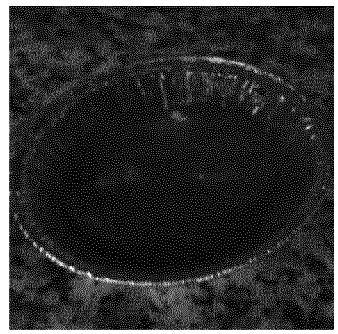
Figures 1, 2, 3, 4, 5, 6, 7, 8, 9, 10, 11, 12, 13, 14, 15, 16, 17, 18, 19, 20:
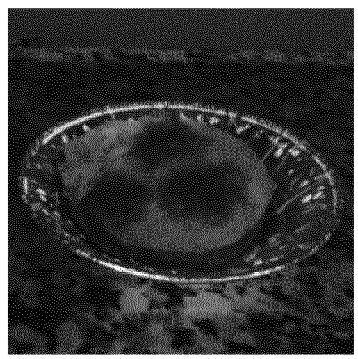
Figures 1, 2, 3, 4, 5, 6, 7, 8, 9, 10, 11, 12, 13, 14, 15, 16, 17, 18, 19, 20, 21:
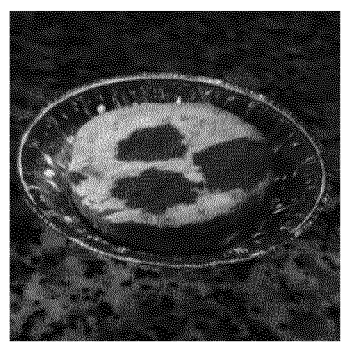
Figures 1, 2, 3, 4, 5, 6, 7, 8, 9, 10, 11, 12, 13, 14, 15, 16, 17, 18, 19, 20, 21, 22:
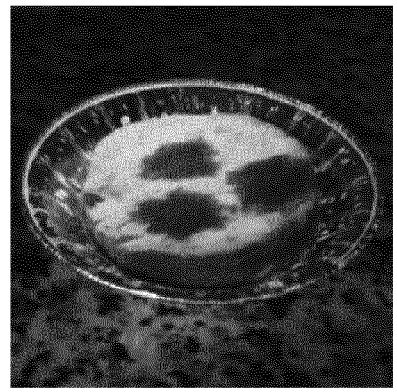
Figures 1, 2, 3, 4, 5, 6, 7, 8, 9, 10, 11, 12, 13, 14, 15, 16, 17, 18, 19, 20, 21, 22, 23:
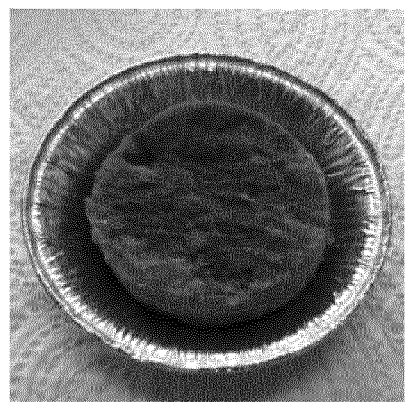
Figures 1, 2, 3, 4, 5, 6, 7, 8, 9, 10, 11, 12, 13, 14, 15, 16, 17, 18, 19, 20, 21, 22, 23, 24:
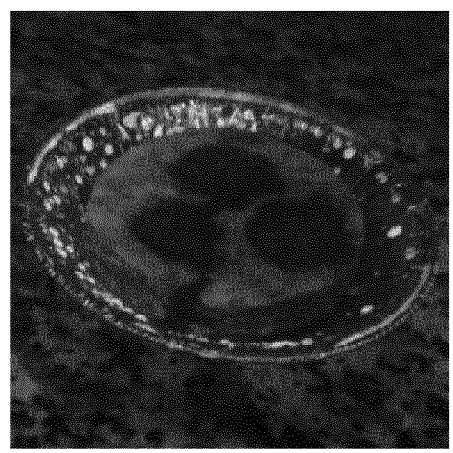
Figures 1, 2, 3, 4, 5, 6, 7, 8, 9, 10, 11, 12, 13, 14, 15, 16, 17, 18, 19, 20, 21, 22, 23, 24, 25:
Figures 1, 2, 3, 4, 5, 6, 7, 8, 9, 10, 11, 12, 13, 14, 15, 16, 17, 18, 19, 20, 21, 22, 23, 24, 25, 26:
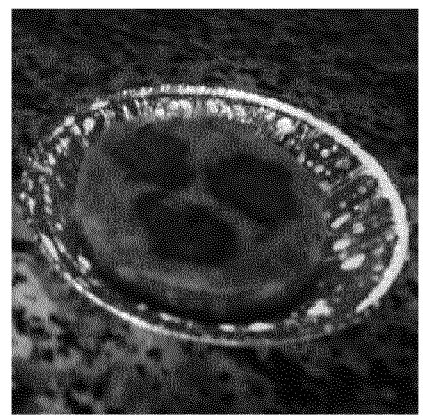
Figures 1, 2, 3, 4, 5, 6, 7, 8, 9, 10, 11, 12, 13, 14, 15, 16, 17, 18, 19, 20, 21, 22, 23, 24, 25, 26, 27:
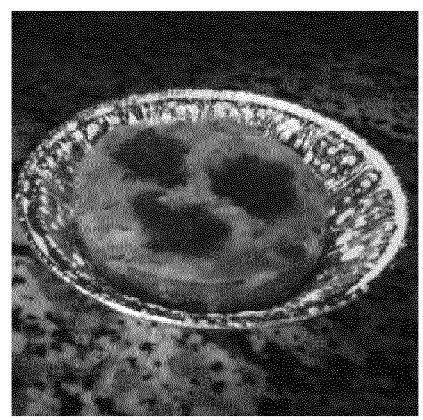
Figures 1, 2, 3, 4, 5, 6, 7, 8, 9, 10, 11, 12, 13, 14, 15, 16, 17, 18, 19, 20, 21, 22, 23, 24, 25, 26, 27, 28:
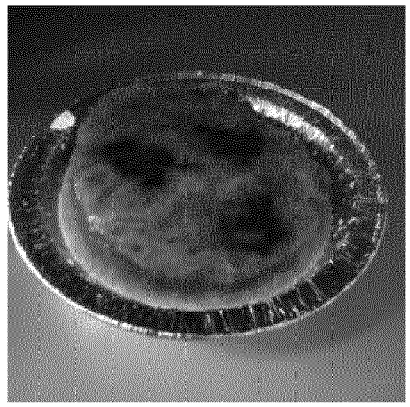
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
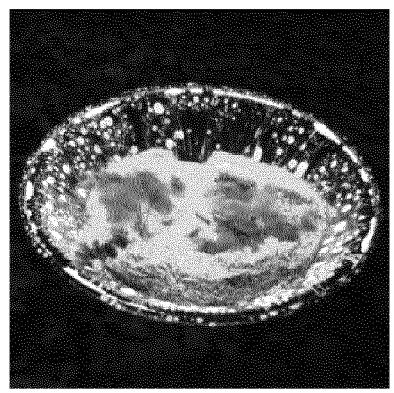
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30:
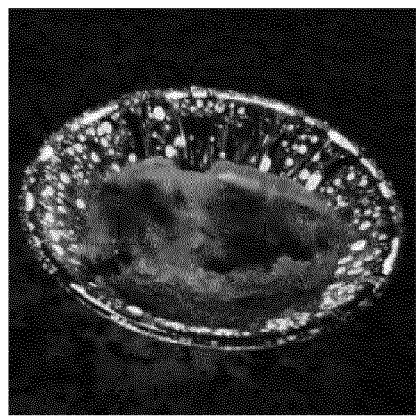
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31:
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
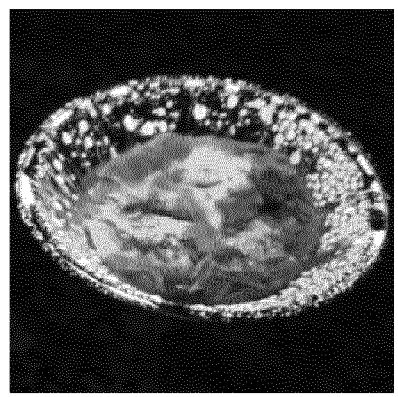
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
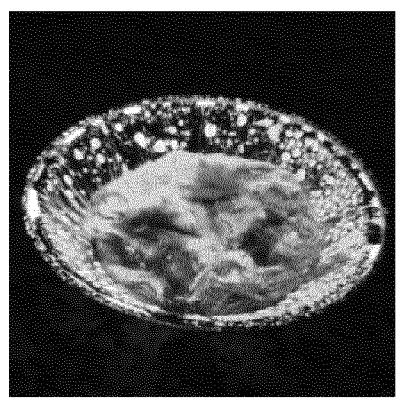
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
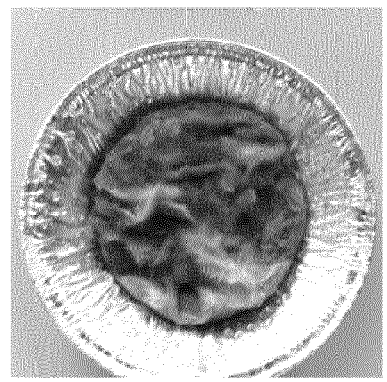
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
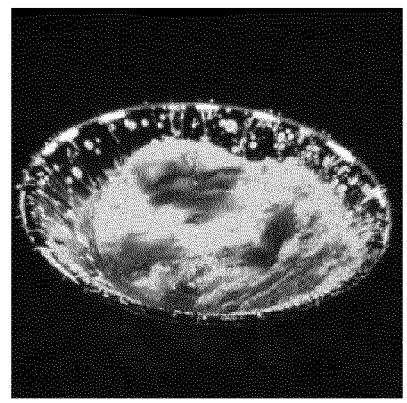
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
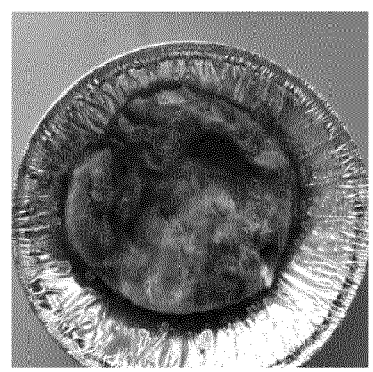
Figures 1, 2:
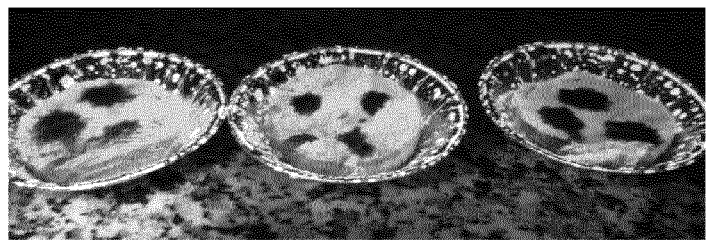
Figure 2:
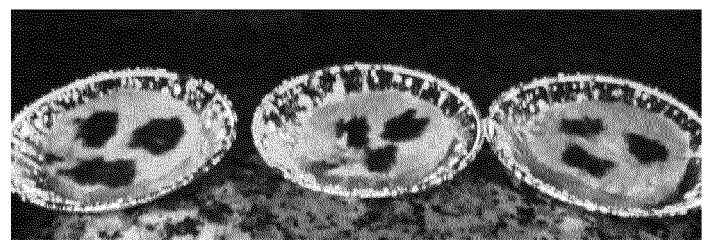
Figures 2, 3:
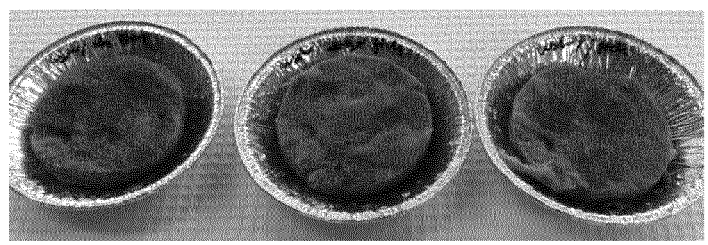
Figures 2, 3, 4:
Figures 1, 3:
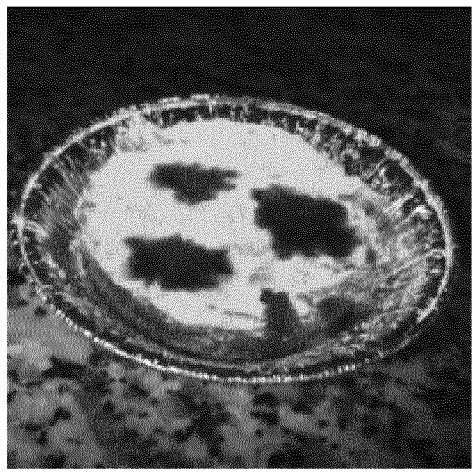
Figures 2, 3:
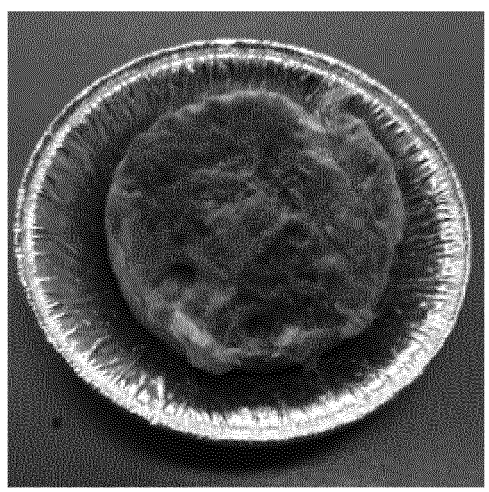
Figures 1, 4:
Figures 2, 4:
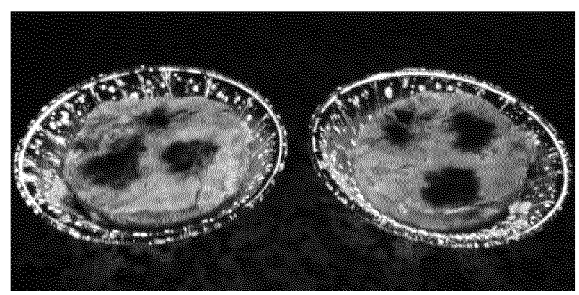
Figures 3, 4:
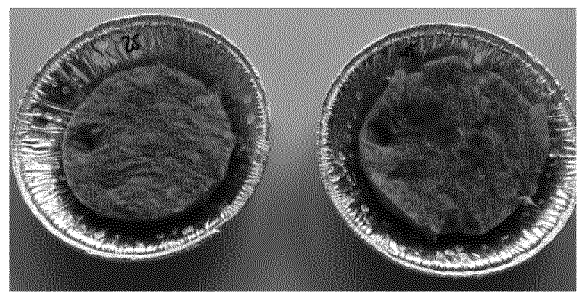
Figures 1, 5:
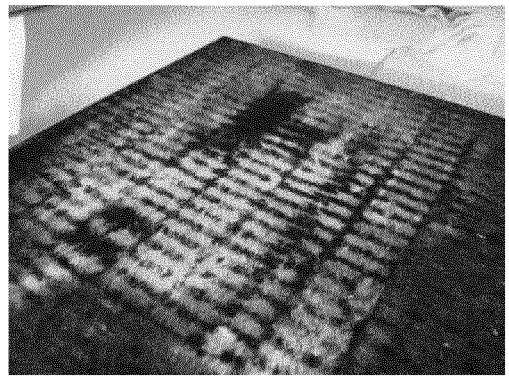
Figures 2, 5:
Figures 3, 5:
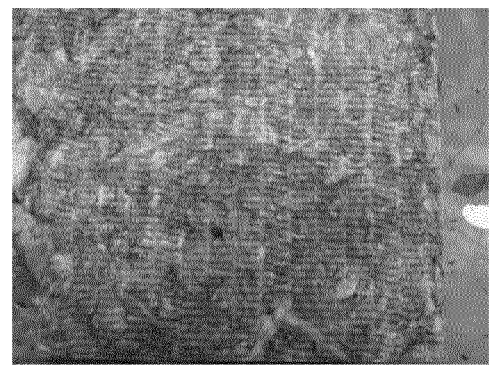
Figures 4, 5:
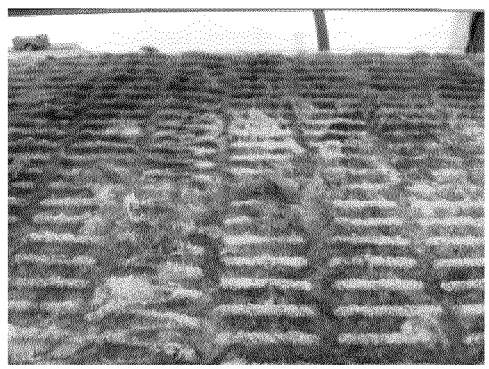
Figure 5:
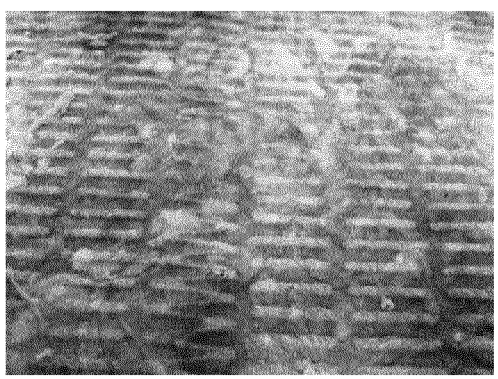
Figures 5, 6:
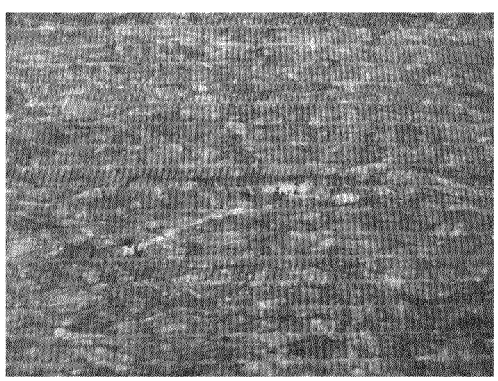
Figures 5, 6, 7:
Figures 5, 6, 7, 8:
Figures 5, 6, 7, 8, 9:
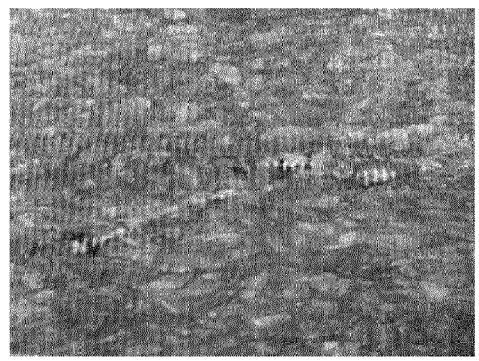
Figures 5, 6, 7, 8, 9, 10:
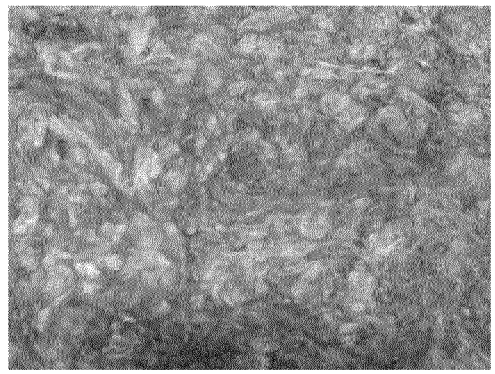
Figures 5, 6, 7, 8, 9, 10, 11:
Figures 5, 6, 7, 8, 9, 10, 11, 12:
Figure 6:
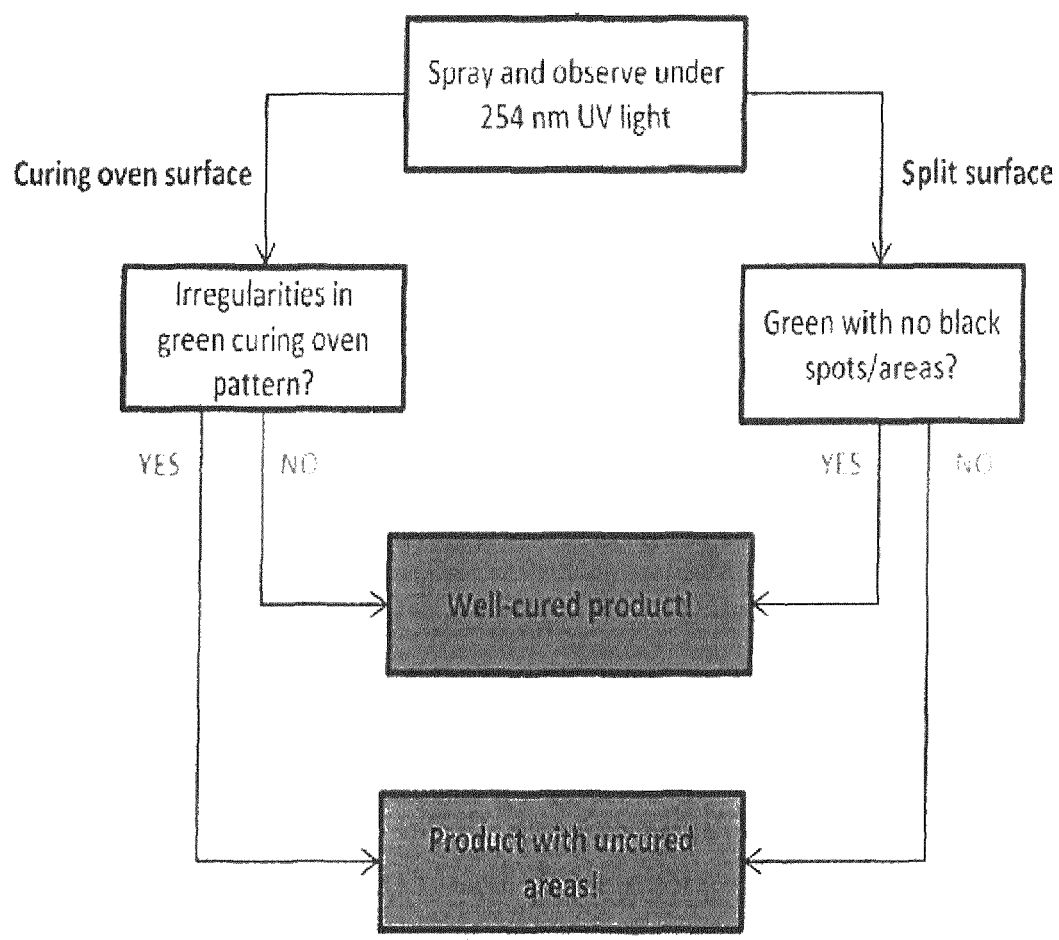

A product not containing uncured regions, as above, produced a regular curing oven pattern of bright green fluorescence on an apparently black background. Areas with uncured regions (some of them visible to the naked eye as "soft bumps") gave irregularities in this pattern (Low density products: FIG. 5-3 before spraying—FIG. 5-4 and FIG. 5-5 after; high-density products: FIG. 5-6 before spraying—FIG. 5-7 and FIG. 5-8 after).

The spray can also be used in daylight (without UV): The areas with uncured regions gave non-colored irregularities on a light green background (FIG. 5-9).

Example 6: Detection of Degree of Curing on Split Surfaces of Stone Wool Products with B1-Sugar-Urea Using 0.01% Fluorescein Sodium Salt The Rockwool products with B1-sugar binder used in example 5 were split open with a saw and inspected on the split surfaces using 0.01% fluorescein sodium salt in 20% aqueous ethanol.

A hardly visible wet spot was identified in the layer directly below an area with uncured regions area on the curing oven surface (FIG. 5-10 before spraying). When sprayed, the areas not containing uncured regions will fluoresce brightly green while the wet spot will appear black (FIG. 5-11).

The spray can also be used in daylight (without UV): The wet spot and saw trail appear dark brown while the background appears light green (FIG. 5-12).

What is claimed is:

1. A method for detecting curing in a mineral fiber product which comprises mineral fibers bonded together with a cured or partly cured thermoset binder, wherein the method comprises bringing the mineral fiber product into contact with a liquid mixture comprising one or more fluorescent compounds and detecting an intensity of fluorescence and/or a pattern of fluorescence or absence of fluorescence on one or more surfaces of the mineral fiber product and/or detecting a color change on one or more surfaces of the mineral fiber product.

2. The method of claim 1, wherein the one or more fluorescent compounds are selected from one or more of xanthenes, acridines, quinine, quinine derivatives, coumarins, aryl sulfonates.

3. The method of claim 1, wherein the method for detecting curing comprises detection of binder distribution anomalies in the mineral fiber product.

4. The method of claim 3, wherein the binder distribution anomalies comprise agglomeration of binder.

5. The method of claim 1, wherein the liquid mixture comprises a fluorescent compound in a concentration of from 0.001 to 1 wt.-%.

6. The method of claim 1, wherein the liquid mixture comprises a fluorescent compound in the form of a solution of from 0.001 to 1 wt.-% of fluorescein sodium salt in one of (1) an aqueous solution of up to 30 wt.-% of one or more $C_1$ to $C_4$ alcohols, (2) an aqueous solution of a detergent, (3) water.

7. The method of claim 6, wherein the liquid mixture comprises from 0.01 to 1 wt.-% of fluorescein sodium salt.

8. The method of claim 6, wherein the one or more $C_1$ to $C_4$ alcohols comprise ethanol and/or isopropanol.

9. The method of claim 1, wherein the mineral fiber product comprises mineral fibers bonded together by a cured or partly cured thermoset binder, the non-cured binder comprising a phenol-formaldehyde based resol and optionally, a sugar component.

10. The method of claim 1, wherein the mineral fiber product comprises mineral fibers bonded together by a cured or partly cured thermoset binder, the non-cured binder comprising (1) a water-soluble binder component obtainable by reacting at least one alkanolamine with at least one polycarboxylic acid or anhydride and, optionally, treating the reaction product with a base; (2) a sugar component; and optionally, (3) urea.

11. The method of claim 1, wherein the mineral fiber product comprises mineral fibers bonded together by a cured or partly cured thermoset binder, the non-cured binder comprising (a) a sugar component, and one or both of (b) a polycarboxylic acid component, and (c) a component selected from amine compounds, ammonia, ammonium salts of a polycarboxylic acids.

12. The method of claim 11, wherein the sugar component is selected from sucrose, reducing sugars, poly-carbohydrates, and mixtures thereof.

13. The method of claim 1, wherein the mineral fiber product comprises man-made vitreous fibers selected from stone fibers, mineral fibers, slag fibers, basalt fibers, glass fibers.

14. The method of claim 1, wherein bringing the mineral fiber product into contact with a liquid mixture comprising a fluorescent compound and detecting the intensity of fluorescence and/or the pattern of fluorescence and/or the absence of fluorescence on one or more surfaces of the mineral fiber product and/or detecting a color change on one or more surfaces of the mineral fiber product are performed immediately after curing and cooling of the binder in the mineral fiber product.

15. The method of claim 1, wherein detecting the intensity of fluorescence and/or the pattern of fluorescence on one or ore surfaces of the mineral fiber product and/or detecting a color change on one or more surfaces of the mineral fiber product takes place by visual inspection.

16. The method of claim 1, wherein detecting the intensity of fluorescence and/or the pattern of fluorescence on one or more surfaces of the mineral fiber product takes place under irradiation with UV light.

17. The method of claim 1, wherein the mixture comprising one or more fluorescent compounds is brought into contact with the mineral fiber product by spraying the liquid mixture onto one or more surfaces of the mineral fiber product.

18. The method of claim 1, wherein the mixture comprising one or more fluorescent compounds is brought into contact with one or more of the outer surfaces of the mineral fiber product.

19. The method of claim 1, wherein the mixture comprising one or more fluorescent compounds is brought into contact with a split surface of the mineral fiber product, the one or more split surfaces resulting from cutting the mineral fiber product.

20. A reagent for the detection of curing and/or binder distribution anomalies in a mineral fiber product, wherein the reagent comprises a solution of from 0.001 to 1 wt.-% fluorescein sodium salt in (1) an aqueous solution of from 1 to 30 wt.-% of one or more $C_1$ to $C_4$ alcohols or (2) an aqueous solution comprising a detergent.

* * * * *